United States Patent [19]
Kay et al.

[11] Patent Number: 6,107,027
[45] Date of Patent: *Aug. 22, 2000

[54] RIBOZYMES FOR TREATING HEPATITIS C

[75] Inventors: Mark A. Kay; Andre Lieber, both of Seattle, Wash.

[73] Assignee: University of Washington, Seattle, Wash.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/534,220

[22] Filed: Sep. 11, 1995

Related U.S. Application Data

[63] Continuation-in-part of application No. 08/476,257, Jun. 7, 1995, abandoned, which is a continuation-in-part of application No. 08/357,508, Dec. 14, 1994, abandoned.

[51] Int. Cl.[7] .............................. C07H 21/04; C12Q 1/68; A61K 35/00; C12N 15/85
[52] U.S. Cl. ........................ 435/6; 435/91.31; 435/320.1; 435/366; 536/23.1; 536/24.5
[58] Field of Search ........................ 435/6, 91.31, 310.1, 435/240.2, 366; 576/23.1, 23.2, 24.5; 514/44

[56] References Cited

U.S. PATENT DOCUMENTS

| | | | |
|---|---|---|---|
| 4,861,719 | 8/1989 | Miller | 435/236 |
| 4,987,071 | 1/1991 | Cech et al. | 435/91.31 |
| 5,124,263 | 6/1992 | Temin et al. | 435/349 |
| 5,219,740 | 6/1993 | Miller et al. | 435/69.6 |
| 5,350,671 | 9/1994 | Houghton et al. | 435/5 |
| 5,354,855 | 10/1994 | Cech et al. | 536/24.1 |
| 5,399,346 | 3/1995 | Anderson et al. | 424/93.21 |
| 5,436,146 | 7/1995 | Shenk et al. | 435/457 |
| 5,610,054 | 3/1997 | Draper | 435/363 |

FOREIGN PATENT DOCUMENTS

| | | |
|---|---|---|
| 0558944 | 9/1993 | European Pat. Off. . |
| 2 212 511 | 7/1989 | United Kingdom . |
| WO 92/12242 | 7/1992 | WIPO . |
| 9323569 | 11/1993 | WIPO . |
| WO 94/02601 | 2/1994 | WIPO . |
| WO 94/20146 | 9/1994 | WIPO . |
| WO 94/26915 | 11/1994 | WIPO . |
| WO 94/27556 | 12/1994 | WIPO . |
| WO 94/29471 | 12/1994 | WIPO . |
| WO 95/19429 | 7/1995 | WIPO . |
| WO 96/01314 | 1/1996 | WIPO . |
| WO 96/01315 | 1/1996 | WIPO . |

OTHER PUBLICATIONS

Stull et al. Pharm Res 12:465–483 (1995).
Sokol et al. Transgenic Research 5:363–371 (1996).
Branch TIBS 23:45–50, 1998.
Barr et al., "Strain Related Variations in Adenovirally Mediated Transgene Expression from Mouse Hepatocytes In Vivo: Comparisons Between Immunocompetent and Immunodeficient Inbred Strains," *Gene Ther.* 2:151–155 (1995).
Cech, "Ribozyme Engineering," *Curr. Op. Structural Biol.* 2:605–609 (1992).
Fausto, "Hepatocyte Differentiation and Liver Progenitor Cells," *Curr. Op. Cell Biol.* 2:1036–1042 (1990).
Frankel (ed.), *Genetically Engineered Toxins*, Marcel Dekker, Inc. (1992).
Gorlich et al., "A Protein of the Endoplasmic Reticulum Involved Early in Polypeptide Translocation," *Nature* 357:47–52 (1992).
Grable et al., "cis and trans Requirements for the Selective Packaging of Adenovirus Type 5 DNA," *J. Virol.* 66:723–731 (1992).
Graham and Prevec, "Manipulation of Adenovirus Vectors," *Methods in Molecular Biology: Gene Transfer and Expression Protocols*, The Humana Press 7:109–128 (1991).
Grundmann et al., *Liver Regeneration After Experimental Injury* Lesch & Reuter (eds.), NY: Stratton Intercontinental Medical Book Co. (1973).
Guerrier–Takada et al., "The RNA Moiety of Ribonuclease P is the Catalytic Subunit of the Enzyme," *Cell* 35:849 (1983).
Hampel et al., "RNA Catalytic Properties of the Minimun (−) sTRSV Sequence," *Biochem.* 28:4929–4933 (1989).
Hampel et al., "'Hairpin' Catalytic RNA Model: Evidence for Helices and Sequence Requirement for Substrate RNA," *Nucl. Acids. Res.* 18(2):299–304 (1990).
Heckel et al., "Neonatal Bleeding in Transgenic Mice Expressing Urokinase–Type Plasminogen Activator," *Cell* 62:447–456 (1990).
Hofmann et al., "Efficient Gene Transfer into Human Hepatocytes by Baculovirus Vectors," *Proc. Natl. Acad. Sci. USA* 92:10099–10103 (1995).
Kay et al., "Hepatic Gene Therapy: Persistent Expression of Human α1–Antitrypsin in Mice after Direct Gene Delivery In Vivo," *Hum. Gene Ther.* 3:641–647 (1992).
Kay et al., "In vivo Hepatic Gene Therapy: Complete Albeit Transient Correction of Factor IX Deficiency in Hemophilia B Dogs," *Proc. Natl. Acad. Sci. USA* 91:2353–2357 (1994).
Kay et al., "In Vivo Gene Therapy of Hemophilia B: Sustained Partial Correction in Factor IX–Deficient Dogs," *Sci.* 262:117–119 (1993).
Ledley et al., "Hepatic Gene Therapy: Present and Future," *Hepatol.* 18(5):1263–1273 (1993).
Li et al., "Assessment of Recombinant Adenoviral Vectors for Hepatic Gener Therapy," *Human Gene Ther.* 4:403–409 (1993).

(List continued on next page.)

*Primary Examiner*—Robert A. Schwartzman
*Assistant Examiner*—Andrew Wang
*Attorney, Agent, or Firm*—Campbell & Flores LLP

[57] ABSTRACT

Adenoviral vectors are used for high efficiency transduction of ribozymes specific for hepatitis C virus RNA. Hepatocytes are transduced with a recombinant adenovirus vector that expresses a ribozyme capable of specifically cleaving HCV RNA. The compositions and methods thus provide new means for treating HCV, and further provide transgenic non-human animals having human hepatocytes which are useful in models of HCV disease for developing therapeutic and preventative agents.

19 Claims, 3 Drawing Sheets

OTHER PUBLICATIONS

Miller, "Progress Toward Human Gene Therapy," *Blood* 76:271–278 (1990).

Miller et al., "Gene Transfer by Retrovirus Vectors Occurs Only in Cells That are Actively Replicating at the Time of Infection," *Mol. Cell. Biol.* 10:4239–4242 (1990).

Miller, "Human Gene Therapy Comes of Age," *Nature* 357:455–460 (1992).

Nagai et al., "Molecular Cloning of cDNA Coding for Human Preprourokinase," *Gene* 36:183–188 (1985).

Okamoto et al., "Full–Length Sequence of a Hepatitis C Virus Genome Having Poor Homology to Reported Isolates: Comparative Study of Four Distinct Genotypes," *Virol.* 188:331–341 (1992).

Pelham, "Evidence that Luminal ER Proteins are Sorted From Secreted Proteins in a Post–ER Compartment," *EMBO J.* 7:913–918 (1988).

Stratford–Perricaudet et al., "Widespread Long–term Gene Transfer to Mouse Skeletal Muscles and Heart," *J. Clin. Invest.* 90:626–630 (1992).

Strubin et al., "Two Forms of the Ia Antigen–Associated Invariant Chain Result from Alternative Initiations at Two In–Phase AUGs," *Cell* 47:619–625 (1986).

Yang et al., "Cellular Immunity to Viral Antigens Limits El–deleted Adenoviruses for Gene Therapy," *Proc. Natl. Acad. Sci. USA* 91:4407–4411.

Yoshioka et al., "Detection of Hepatitis C Virus by Polymerase Chain Reaction and Response to Interferon–α Therapy: Relationship to Genotypes of Hepatitis C Virus," *Hepatol.* 16:293–299 (1992).

Perrotta and Been, "Cleavage of Oligoribonucleotides by a Ribozyme Derived from the Hepatitis δ Virus RNA Sequence," *Biochem.* 31:16–21 (1992).

Pozzato et al., "Different Genotypes of Hepatitis C Virus are Associated With Different Severity of Chronic Liver Disease," *J. Med. Virol.* 43:291–296 (1994).

Rhim et al., "Replacement of Diseased Mouse Liver by Hepatic Cell Transplantation," *Sci.* 263:1149–1152 (1994).

Rossi et al., "Ribozymes as Anti–HIV–1 therapeutic Agents: Principles, Applications, and Problems," *AIDS Res. Hum. Retrovir.* 8:183 (1992).

Sandgren et al., "Complete Hepatic Regeneration After Somatic Deletion of an Albumin–Plasminogen Activator Transgene," *Cell* 66:245–256 (1991).

Schutze et al., "An N–terminal Double–Arginine Motif Maintains Type II Membrane Proteins in the Endoplasmic Reticulum," *EMBO J.* 13:1696–1705 (1994).

Shenk et al., "Genetic Analysis of Adenoviruses," *Curr. Top. Microbiol. Immunol.* 111:1–39 (1984).

George et al., "Ribozyme Mediated Cleavage of Hepatitis B Virus Surface Antigen mRNA," *J. Cell. Biochem.* Suppl. 17E:212, abs. S407 (1993).

Ledley, "Hepatic Gene Therapy: Present and Future," *Hepatolgy* 18 (5):1263–1273 (1993).

Marshall, "Gene Therapy's Growing Pains," *Sci.* 269:1050–1055 (1995).

Rhim et al., "Replacement of Diseased Mouse Liver by Hepatic Cell Transplantation," 263:1149–1152 (1994).

Shih et al., "A Novel Clamp–Like Structure Enables Retargeting of a Ribozyme Derived from the Antigenome of Hepatitis Delta Virus and Trans–Cleavage of Heterologous RNA," *J. Cell. Biochem.* 17E:214, abs. S416 (1993).

RIBOZYMES FOR TREATING HEPATITIS C

RELATED APPLICATION

This is a continuation-in-part of U.S. Ser. No. 08/476,257, filed Jun. 7, 1995, now abandoned, which is a continuation-in-part of U.S. Ser. No. 08/357,508, filed Dec. 14, 1994, now abandoned, each of which is incorporated herein by reference.

GOVERNMENT SUPPORT

Certain embodiments of the invention described herein were made in the course of work supported by the National Institutes of Health pursuant to grant no. DK47754. Therefore, the U.S. Government has certain rights in this invention.

BACKGROUND OF THE INVENTION

The major etiological agent of posttransfusional and community acquired non-A non-B hepatitis has been identified as hepatitis C virus (HCV). Choo et al., *Science* 244: 359–362 (1989). At present, intravenous drug abuse is the most important risk factor for transmission of HCV. However, different epidemiological studies have revealed that for up to 20 to 40% of patients chronically infected with HCV, no known risk factors for HCV can be demonstrated. Alter et al., *N. Engl. J. Med.* 327:1899–1905 (1992).

Although the disease associated with HCV may be benign, persistent infection may lead to liver cirrhosis and hepatocellular carcinoma (Saito et al., *Proc. Natl. Acad. Sci. USA* 87:6547–6549), although the mechanism of cellular transformation is unknown. HCV disease can be manifested as acute viral hepatitis which is usually clinically mild, but in other cases the disease may develop into a severe or fulminant hepatitis. Chronic HCV hepatitis is believed to occur more frequently than with hepatitis B virus, especially following posttransfusional acute hepatitis C disease, i.e., in about 54% of cases. Hollinger, in *Fields Virology*, 2d ed., Chpt. 78, eds. B. Fields and D. Knipe, Raven Press, N.Y. (1990).

On the basis of sequence homology, the single-stranded positive-sense RNA enveloped HCV virus has been provisionally classified as a separate genus of the family Flaviviridae. Miller and Purcell, *Proc. Natl. Acad. Sci. USA* 87:2057–2061 (1990). The HCV genome is about 10 kb in length and it encodes a single polyprotein of about 3,000 amino acids that includes structural and nonstructural proteins that are processed by cellular and virus-encoded proteinases. The processed gene products include a putative core (C), three putative envelopes (E1, E2 type A, and E2 type B), and six nonstructural (NS) proteins (NS2, NS3, NS4A, NS4B, NS5A, and NS5B). Representative sequences of HCV strains are described in U.S. Pat. No. 5,350,671 to Houghton et al., incorporated herein by reference.

Comparative sequence analysis of complete HCV genomes (Okamoto et al., *Virology* 188:331–341 (1992)) and PCR fragments from various genomic regions has shown that HCV may be grouped into distinct but related genotypes. At present, six major genotypes (1–6) with numerous subtypes (e.g., 1a, 1b; 2a, 2b, 3a, 5a) have been identified. Three additional types have been recently identified but are apparently limited in geographic distribution. Some genotypes have been associated with severity of disease (Pozzato et al., *J. Med. Virol.* 43:291–296 (1994)) and responsiveness to interferon therapy (Yoshioka et al., *Hepatology* 16:293–299 (1992)).

To date, treatment of HCV infection has primarily been with alpha-interferon. In some instances liver transplantation has been performed for end-stage hepatic deficiency, but invariably the transplanted liver also becomes infected with HCV and ultimately fails.

Gene therapy involves the introduction of genetic material into the cells of an organism to treat or prevent a disease. The material transferred can be from a few nucleotides to a few genes in size. Gene therapy is potentially useful in the treatment and prevention of acquired diseases, such as infectious diseases and cancer. A variety of cell types have been targeted in somatic cell gene therapy systems, including hematopoietic cells, skin fibroblasts and keratinocytes, hepatocytes, endothelial cells, skeletal and smooth muscle cells, and lymphocytes, each with varying success.

Methods for gene therapy involving hepatocytes have relied on gene transfer ex vivo, i.e., inserting genes into hepatocytes which have been removed from a patient which are then reimplanted into the liver, or in vivo, i.e., gene transfer directly into the liver. For ex vivo methods, gene transfer into cells must occur at high efficiency to obtain suitable numbers of cells for transplantation, because primary cultures of hepatocytes cannot be expanded. Long term expression in transduced hepatocytes has been accomplished with retroviral vectors, but the efficiency of transduction is relatively low (the retrovirus infects only dividing cells; Miller et al., *Mol. Cell. Biol.* 10:4239–4242 (1990)), and the protein may not be expressed in therapeutically or prophylactically effective amounts. In one ex vivo method approximately 20% of a patient's liver is surgically removed, the cells are then transduced with the retroviral vector, and then implanted back into the patient. This approach suffers from obvious disadvantages of surgical procedures and a low efficiency of transduction and expression of the gene product of interest.

Similarly, an in vivo approach to transducing hepatocytes with retroviral vectors involves first performing a partial hepatectomy followed by portal vein infusion of the vector. The removal of the majority of the liver is needed to stimulate liver regeneration so that the retrovirus will integrate into the cells' genomes. As with the ex vivo approach, this method suffers from requiring a major surgical procedure and under the best of conditions only about 1% of the liver mass contains the genetically modified vectors.

As an alternative to retroviral-mediated hepatic gene therapy, the adenovirus presents a transfer vector that can infect nonreplicating cells at high efficiency. Adenoviral DNA remains extra-chromosomal and thus is slowly lost from transduced hepatocytes over a period of several months. Li et al., *Human Gene Ther.* 4: 403–409 (1993); Kay et al., *Proc. Natl. Acad. Sci. USA* 91: 2353–2357 (1994). Additionally, a substantial portion of the adenovirus is taken up by organs and tissues other than the liver, which may raise issues of safety. (Smith et al., 1993, and Kay et al., ibid.). And, as adenovirus stimulates the production of neutralizing antibodies in an infected host, patients who have been naturally infected with adenovirus may be resistant to gene therapy using this vector, or secondary transductions may be prevented by the presence of antibodies produced in response to a primary transduction (Smith ibid., Kay, ibid.).

There remains a significant need in the art for compositions useful in treating hepatitis C infection and methods for their delivery to HCV-infected cells of the liver. Desirably, the compositions and methods should effectively reduce or eradicate HCV from infected cells, or should significantly impair the ability of the virus to replicate, thereby preventing further dissemination of the disease. The compositions should be inherently specific for HCV and of negligible toxicity. Quite surprisingly, the present invention fulfills these and other related needs.

SUMMARY OF THE INVENTION

Methods and compositions are provided for producing ribozymes targeted to HCV gene products of interest in an HCV-infected or susceptible mammal, thereby inhibiting or preventing HCV infection and spread. In one aspect the methods comprise transducing cells, especially hepatocytes, with a recombinant adenovirus which encodes a ribozyme specific for hepatitis C virus RNA. When the sequence encoding the ribozyme is expressed, HCV RNA in the infected cell is inhibited or infection is prevented. Preferably the ribozyme is a hammerhead ribozyme, and specifically cleaves hepatitis C RNA in a HCV 5'non-coding sequence, core sequence, or NS-5 sequence. Administration may be performed with hepatocytes from an HCV-infected individual, i.e., ex vivo administration, or administered to the individual. When administered to an individual, typically administration will be by infusion, such as via the portal vein or bile duct. Typically the recombinant adenovirus is administered to the hepatocytes in an amount and for a time sufficient to eradicate hepatitis C virus from the hepatocytes, preferably from about 10 to 100 adenovirus particles per hepatocyte. For increased activity against HCV, the vector(s) may encode two or more ribozymes specific for different regions or strands of HCV RNA.

In another aspect the invention provides recombinant adenovirus encoding at least one ribozyme specific for HCV RNA, and sometimes will encode two different ribozymes specific for HCV RNA. Preferably the recombinant adenovirus encodes a hammerhead ribozyme specific for HCV. In yet other embodiments a ribozyme specific for HCV RNA targets an HCV sequence that corresponds to a cDNA sequence comprising CGGGAGGTCTCGTA [Seq. ID:1] (nucleotide 317 to 332), GCACCATGAGCACGAA [Seq. ID:2] (nucleotide 337 to 352), CTAAACCTCAAAGAAA [Seq. ID:3] (nucleotide 355 to 370), CCAACCGTCGC-CCACAG [Seq. ID:4] (nucleotide 385 to 401), CCCACAG-GACGTCAAG [Seq. ID:5] (nucleotide 385 to 410), or GGTAAGGTCATCGATA [Seq. ID:6] (nucleotide 699 to 714).

DESCRIPTION OF THE SPECIFIC EMBODIMENTS

The present invention provides compositions and methods for treating or preventing hepatitis C infection using therapeutic ribozymes. The ribozymes can be administered in a variety of ways, including by gene therapy targeted to the liver of an individual exposed to or infected by HCV.

A ribozyme of the invention targets the HCV RNA genome and RNA transcripts and copies thereof. Each ribozyme molecule contains a catalytically active segment capable of cleaving the plus or minus strand of HCV RNA, and further comprises flanking sequences having a nucleotide sequence complementary to portions of the HCV RNA. The flanking sequences serve to anneal the ribozyme to the RNA in a site-specific manner. Absolute complementarity of the flanking sequences to the target HCV sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific HCV RNA plus or minus strand target, and also has enzymatic activity that is active to cleave and/or splice RNA in that target, thereby altering the target molecule. By reference to HCV plus strand is meant one having the same polarity as viral mRNA and containing codon sequences that can be translated into viral protein. The minus strand is a noncoding strand that must be copied by an RNA-dependent polymerase to produce a translatable mRNA.

In preferred embodiments of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8: 183 (1992), hairpin motifs are described by Hampel et al., *Biochem.* 28:4929 (1989) and Hampel et al., *Nucl. Acids Res.* 18: 299 (1990), the hepatitis delta virus motif is exemplified in Perrotta and Been, *Biochem.* 31: 16 (1992), an RNAseP motif is described in Guerrier-Takada et al., *Cell* 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target HCV RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 9 to 12, and results in base pairing to the substrate sequence immediately upstream and downstream of the plus or minus strand HCV RNA sequences which comprise the cleavage site.

To select therapeutically useful ribozymes specific for HCV RNA, ribozymes are selected and expressed in whole cells. An optimized expression cassette for the ribozyme can be used where the sequence is embedded in a stable loop region which, in turn, is part of an adenoviral va RNA, so that a catalytic secondary structure can form independently from the surrounding RNA of the expressed RNA. A library of ribozymes flanked by random sequences are cloned into the loop region of the expression cassette. Ribozymes are selected from the library using the HCV RNA target sequence itself. Using this strategy a ribozyme is selected for cleavage sites that are accessible within target HCV RNA and that have structures that permit efficient cleavage. Ribozymes are selected against conserved regions of the HCV genome to be effective against as many HCV strains as possible and to reduce the opportunity for escape variants. These regions include the plus or minus strands of the 5' noncoding region and those coding for the core protein and NS5 RNA polymerase. To confirm the effectiveness of the ribozymes in mammalian cells, HCV cDNA is transduced into hepatoma cells to produce intact HCV RNA. Cells which stably produce high level expression of HCV RNA are selected and then transfected with the ribozyme expression cassette. The resulting cleavage of HCV RNA by a ribozyme produces a 5'OH group and a 2'–3' cyclic phosphate group, thereby creating an unstable molecule and decreasing the HCV mRNA concentration within the cell. Ribozyme producing cell lines are compared for the production of HCV RNA and those ribozymes with optimal activity are selected. Cross-reactivity of the ribozyme with different HCV types can also be determined in this system. Ribozymes directed against different target sites in a particular mRNA can be simultaneously isolated using this procedure. This approach has permitted the selection of ribozymes against HCV RNA which completely eliminate HCV RNA expressed in CHO cells.

The site of cleavage in a target HCV RNA molecule is also dependent on the type of ribozyme, e.g., when the ribozyme is of the hammerhead type, the substrate cleavage site is immediately 3' to the sequence NUH, where N is any nucleotide, U is uridine, and H is any nucleotide except G. Different types of ribozymes can be used to achieve the specific cleavage of the targeted HCV RNA molecule, e.g., different hammerhead ribozymes (at least 14 different members of this class), the larger Group I introns, RNAse P (which targets tRNA), hairpin ribozymes, hepatitis delta virus ribozyme, etc.

As mentioned above, the HCV RNA target region is typically one that is substantially conserved among the prevalent strains of HCV. These regions include the 5' noncoding region, the core protein, and the nonstructural proteins NS-2, NS-3 (helicase), NS-4, NS-5 (RNA polymerase), and conserved regions of E1 (gp30) and NS-1 (gp72). Representative examples of HCV ribozyme target sequences include, for HCV types 1 a and 1 b (where putative cleavage sites are indicated by a "–"), ribozyme 1 (Rz1): CGGGAGGTCTCGTA [Seq. ID:1] (5' UTR, nucleotides 317 to 332; plus strand), Rz2: GCACCATGAGCAC-GAA [Seq. ID:2] (nucleotide 337 to 352; minus strand), Rz5: CTAAACCTCAAAGAAA [Seq. ID:3] (core, nucleotide 355 to 370; plus strand), Rz4: CCAACCGTCGCCCA-CAG [Seq. ID:4] (core, nucleotide 385 to 401; plus strand), Rz3: CCCACAGGACGTCAAG [Seq. ID:5] (core, nucleotide 385 to 410; minus strand), and Rz6: GGTAAGGT-CATCGATA [Seq. ID:6] (core, nucleotide 699 to 714; plus strand).

A sequence comprising or encoding said ribozyme or a combination of ribozymes targeted to different portions of the HCV RNA can be delivered in a wide variety of ways to HCV-infected or HCV-susceptible cells to interrupt or prevent HCV infection. The ribozyme can be administered as RNA or expressed from an expression vector. The ribozyme can be administered ex vivo, i.e., contacted with cells that have been removed from an infected individual, treated and returned, or the ribozyme can be administered in vivo. Delivery can be via an appropriate delivery vehicle, e.g., a liposome, a controlled release vehicle, by use of iontophoresis, electroporation or ion paired molecules, or covalently attached abducts, and other pharmacologically acceptable methods of delivery. Preferably a carrier provides a means to accumulate the ribozyme at the primary site of HCV infection, i.e., the liver. The ribozyme delivery vehicle can be designed to serve as a slow release reservoir or to deliver its contents directly to the target cell. WO 94/16736 describes a process for evolving RNA molecules to bind receptors on liver cells, to which RNA a ribozyme of the present invention may be tethered for targeting purposes. Examples of ribozyme delivery vehicles include liposomes, hydrogels, cyclodextrins, biodegradable nanocapsules, and bioadhesive microspheres. Liposomes can readily be targeted to the liver for delivery of RNA to infected hepatocytes. In a preferred embodiment the anti-HCV ribozyme is administered via an expression vector that is suitable for delivery and expression of an oligonucleotide comprising said ribozyme in a mammalian host cell.

Routes of ribozyme administration include intramuscular, aerosol, intravenous, parenteral, intraperitoneal, etc. The specific delivery route for a selected ribozyme will depend on a variety of factors, such as the form of the ribozyme, the intended target, the stage of disease, etc. For example, while unmodified ribozyme is taken up by cells, modifications can be made to enhance cellular uptake, e.g., by reducing the ribozyme's charge to produce a molecule which is able to diffuse across the cell membrane. The structural requirements necessary to maintain ribozyme catalytic activity are generally recognized in the art, as described in, e.g., Cech, Curr. Op. Structural Biol. (1992), which is incorporated herein by reference. Ribozyme modifications to enhance cellular delivery can also be designed to reduce susceptibility to nuclease degradation.

The dosage of ribozyme will also depend on a variety of factors, such as the form of the ribozyme, the route of administration, the severity of infection or stage of disease, the general condition of the patient being treated, and thus can vary widely. Generally the dosage of ribozyme will be between about 10 $\mu$g–200 mg/kg of body weight per day and result in therapeutic or prophylactic levels within the targeted cells sufficient to inhibit or eradicate HCV from the cells. Establishment of therapeutic or prophylactic levels of ribozyme within an HCV-infected cell depends upon, e.g., the rate of uptake (or expression by a particular vector), and rate at which the ribozyme is degraded. The duration of treatment may extend throughout the course of HCV infection or disease symptoms, usually at least about 7–30 days, with longer durations being necessary for severe infections. The number and timing of doses can vary considerably, depending on, e.g., the extent of infection, the efficacy of a particular ribozyme or mixture thereof, the delivery vehicle and route of administration, the judgment of the prescribing physician, etc. As used herein, the terms "treatment" or "treating" refer to any ribozyme-based treatment of HCV or related disease, and include: (1) preventing HCV disease from occurring in a subject who does not have the disease or who has not yet been diagnosed as having it, including prophylactic uses to individuals susceptible to or suspected of exposure to HCV; (2) eradicating, inhibiting or arresting the development of HCV infection or related disease; or (3) regressing or reversing the disease.

The ribozymes of the invention may be prepared by chemical synthesis or produced by recombinant vectors according to methods established for the synthesis of RNA molecules. See, e.g., Sambrook et al., *Molecular Cloning, A Laboratory Manual,* 2d ed., Cold Spring Harbor Laboratory Press, Cold Spring Harbor, N.Y. (1989), incorporated herein by reference. The ribozyme sequence may be synthesized, for example, using RNA polymerases such as T7 or SP6. The ribozymes of the invention may be prepared from a corresponding DNA sequence (DNA which on transcription yields a ribozyme) operably linked to an RNA polymerase promoter such as the promoter for T7 RNA polymerase or SP6 RNA polymerase. A DNA sequence corresponding to a ribozyme of the present invention may be ligated into a DNA vector, such as a plasmid, bacteriophage or other virus. Where the transfer vector contains an RNA polymerase promoter operably linked to DNA corresponding to a ribozyme, the ribozyme may be conveniently produced upon incubation with an RNA polymerase. Ribozymes may therefore be produced in vitro by incubation of RNA polymerase with an RNA polymerase promoter operably linked to DNA corresponding to a ribozyme, in the presence of ribonucleotides. In vivo, procaryotic or eucaryotic cells (including mammalian cells) may be transfected with an appropriate vector containing genetic material corresponding to a ribozyme in accordance with the present invention, operably linked to an RNA polymerase promoter such that the ribozyme is transcribed in the host cell. Ribozymes may be directly transcribed in vivo from a transfer vector, or alternatively, may be transcribed as part of a larger RNA molecule. For example, DNA corresponding to ribozyme sequences may be ligated into the 3' end of a carrier gene, for example, after a translation stop signal. Larger RNA molecules may help to stabilize the ribozyme molecules against nuclease digestion within cells. On translation the carrier gene may give rise to a protein, whose presence can be directly assayed if desired, for example, by enzymatic reaction when the carrier gene encodes a enzyme.

In one exemplary method of producing a ribozyme, two synthetic oligonucleotides of complementary sequence are prepared by standard procedures on an automated DNA synthesizer and hybridized together, where one of the oligonucleotides encodes a desired ribozyme. The respective ends of the hybridized oligonucleotides correspond to different restriction enzyme sites and, after appropriate cleavage, the double stranded DNA fragment is cloned into a transfer vector. Where the plasmid vector contains a RNA polymerase promoter upstream from the DNA sequence corresponding to a ribozyme of the present invention, RNA transcripts corresponding to the ribozyme are conveniently prepared either in vitro or in vivo. When in vivo, that is, within the cell or cells of an organism, a transfer vector such as a bacterial plasmid or viral RNA or DNA encoding one or more ribozymes may replicate and/or be transcribed by cellular polymerases to produce ribozyme RNAs which then inactivate a desired target HCV RNA sequence. The transfer vector may become integrated into the genome of the host cell and transcription of the integrated genetic material gives rise to ribozymes which act to inactivate the target HCV RNA.

Accordingly, a viral vector containing a sequence corresponding to a ribozyme of the present invention can be prepared in any of a wide variety of ways. Representative retroviral vectors suitable for use in the present invention are described, for example, in U.S. Pat. Nos. 4,861,719, 5,124, 263 and 5,219,740, Kay et al., *Hum. Gene Ther.* 3: 641–647 (1992) and Kay et al., *Science* 262:117–119 (1993), each of which is incorporated herein by reference. Other vectors may also be employed, particularly for the ex vivo methods described herein, such as DNA vectors, pseudotype retroviral vectors, adenovirus, adeno-associated virus, gibbon ape leukemia vector, VSV-G (e.g., as described in WO 94/29440), VL30 vectors, liposome mediated vectors, and the like.

Because adenovirus is capable of infecting dividing and non-dividing hepatocytes at high efficiency, in a preferred embodiment the vector is an adenovirus (or adeno-associated virus vector). Representative adenoviral vectors which can be used to encode the ribozymes of the present invention are described in Stratford-Perricaudet et al., *J. Clin. Invest.* 90: 626–630 (1992), Graham and Prevec, in Methods in Molecular Biology: Gene Transfer and Expression Protocols, 7: 109–128 (1991) and Barr et al., *Gene Therapy,* 2:151–155 (1995), WO 94/20146, WO 94/26915, and WO94/29471, and adeno-associated vectors are described in U.S. Pat. No. 5,436,146, each of which is incorporated herein by reference. A preferred adenovirus plasmid for producing recombinant adenovirus which drives transcription of a ribozyme of the invention is the pXCJL.1 plasmid described in Spessot et al., *Virology* 168:378–387 (1989), incorporated herein by reference. An adenoviral vector may include essentially the complete adenoviral genome (Shenk et al., *Curr. Top. Micrbiol. Immunol.* 111: 1–39 (1984) or may be a modified adenoviral vector in which at least a portion of the adenoviral genome has been deleted. In a preferred embodiment, the adenoviral vector comprises an adenoviral 5' LTR, an adenoviral 3' ITR, an adenoviral encapsidation signal; at least one DNA sequence encoding a ribozyme of the present invention; and a promoter controlling the transcription of the ribozyme or an RNA polymerase and a promoter controlling the transcription of the RNA polymerase sequence, e.g., T7 polymerase controlled by the PGK promoter. The vector is typically free of at least the majority of adenoviral E1, E2 and E4 DNA sequences.

The vector is preferably packaged into infectious, nonreplicating, recombinant adenoviral particles using, e.g., a helper adenovirus or cell line which provides the necessary encapsidation materials. Preferably the helper virus has a defective encapsidation signal so the helper virus will not encapsidate itself. An example of an encapsidation defective helper virus which may be employed is described in Grable et al., *J. Virol.* 66:723–731 (1992), incorporated herein by reference.

The vector and the encapsidation defective helper virus are transfected into an appropriate cell line for the generation of infectious viral particles. Transfection may take place by electroporation, calcium phosphate precipitation, microinjection, or through proteoliposomes. Examples of appropriate cell lines include, but are not limited to HeLa cells or 293 (embryonic kidney epithelial) cells (ATCC No. CRL 1573). The infectious viral particles (i.e., the adenoviral vector) may then be transduced into eucaryotic cells, such as hepatocytes, whereby the DNA sequence encoding a ribozyme is expressed by the eucaryotic cells in a host.

The viral vector, consisting of infectious, but replication-defective, viral particles, which contain at least one DNA sequence encoding a ribozyme effective against HCV RNA, is administered in an amount effective to inhibit or prevent HCV infection in a host. The vector particles may be administered in an amount from 1 plaque forming unit to about $10^{14}$ plaque forming units, more preferably from about $1 \times 10^6$ plaque forming units to about $1 \times 10^{13}$ plaque forming units. A sufficient number of adenoviral vector particles containing a sequence corresponding to a ribozyme of the invention should be administered to the liver to infect up to at least about 50% of the hepatocytes, usually about 80%, preferably about 95%, and more preferably 99% to 99.99% or more of the hepatocytes in the individual, e.g., typically from about 10 up to about 100 or more adenovirus particles per hepatocyte are administered. The host may be a human or non-human animal host. A preferred non-human animal host is a mammal, more preferably a non-human primate or a non-human mammal having a liver which is comprised at least partially of human hepatocytes, as more fully described herein. The adenovirus vector can be administered by a variety of routes, but typically systemically, such as, for example, by intravenous administration (e.g., peripheral vein injection), by infusion via the portal vein, to the bile duct, intramuscularly, intraperitoneally, or intranasally.

The expression of the ribozyme sequence encoded by the vector can be constitutive or inducible, but preferably is constitutive. As the hepatocytes which express the ribozyme inhibit the proliferation of and are capable of eradicating HCV, virus-free hepatocytes may repopulate the liver. Thus, over a period of days to weeks hepatocytes treated with the anti-HCV ribozyme may repopulate the liver. The entire treatment process itself may be repeated as necessary, understanding that a humoral immune response to certain vectors, e.g., adenovirus vector, may be generated by repeated administration. The immune response may ameliorate the effect of vector administration and thus necessitate administration of larger quantities of the vector, administration of a different vector to which the patient is not immune, delivery of the vector in a manner by which the particles are shielded from the host's immune system, or tolerization of the host's immune system to the vector.

The vector encoding the anti-HCV ribozyme is also used to transduce hepatocytes which have been isolated from a patient. In some cases, e.g., extreme hepatocellular disease, it may be desirable to use hepatocytes which have been isolated from a suitable uninfected donor, i.e., one who is substantially the same or closely related in histocompatibility type, as may be the case for a liver transplant. The transduced hepatocytes may be cultured for up to 5 to 10 days or longer before being administered to the patient, but typically the cells will be administered by infusion, typically via the portal or splenic vein, in single or multiple administrations, within 1–5 days after removal. For ex vivo transduction the viral vector is preferably a retroviral vector, although other vectors may also be used. In the case of liver transplants, the liver may be transduced with the vector, e.g., adenovirus, prophylactically prior to transplant, while in the donor or ex vivo, or after transplant but before HCV infection of the donor liver is substantially established.

The invention also provides non-human mammals with functioning non-native liver, e.g., human, or native liver which expresses a desired gene product. The animals can be used as models for evaluating a wide variety of disease processes and treatments. For example, the animal models can be used to as models of pathogenesis for infections, e.g., viral infections such as hepatitis C or the like, or to determine the effectiveness and safety of treatments described herein for such infections.

In one embodiment the non-human animals of the present invention contain a transgene which encodes a modified non-secreted uPA as described herein, e.g., uPA having a modified C-terminus containing KDEL, uPA having the signal peptide on the N-terminus substituted by the RR retention signal and transmembrane region of the type II transmembrane proteins (Schutze et al., *EMBO J.* 13: 1696–1705 (1994); Gorlich et al., *Nature* 357: 47–52 (1992), or a combination of both C-terminal and N-terminal modifications designed to inhibit secretion of the uPA molecule without substantially adversely affecting hepatotoxic activity. Expression of the modified uPA can be under the control of an inducible or constitutive promoter, e.g., the cytochrome P450 promoter of Jones et al., *Nucl. Acids Res.* Simultaneous with or subsequent to expression of the secretion-impaired uPA transgene, non-native (e.g., human) hepatocytes are implanted in the transgenic mammal, e.g., a nude or immunodeficient scid mice, to reconstitute the mammal's liver with a large proportion of non-native (e.g., human) hepatocytes. The mammal is then used as a model for human hepatitis C infection and its treatment, e.g., with ribozymes against HCV RNA as described herein.

In another embodiment the mammal can be transduced with an adenoviral vector encoding the modified, secretion-impaired uPA or a hepatotoxin which inhibits or kills hepatocytes, and the non-native cells implanted. The mammal's liver is reconstituted with the non-native hepatocytes and the animal used as described above. Typically the hepatotoxin is one such as uPA, or tPA can be used to stimulate hepatocyte regeneration de novo without causing liver damage. The molecule which stimulates hepatocyte regeneration, with or without hepatotoxic activity, should be specific for hepatocytes, or if not specific, should not be secreted by the infected hepatocytes into the bloodstream. A representative example is uPA which has been modified by N-terminal and/or C-terminal modifications as described herein so as to inhibit secretion by the infected host cell. In some cases other toxins may be used, where they are placed under the control of tissue-specific (liver) promoters and are not secreted, or the vectors are specifically targeted to hepatic tissue. These toxins include the cytotoxic domain of bacterial toxins such as Pseudomonas exotoxin A, diphtheria toxin, cholera toxin, shiga and shiga-like toxin, ribosome inactivating toxins derived from plants and fungi (e.g., ricin), hepatocyte growth factor, and others described in *Genetically Engineered Toxins*, ed. A. Frankel, Marcel Dekker, Inc. (1992), incorporated by reference herein.

In the animal model, the sequences encoding the selected ribozymes are placed into adenoviral vectors and used to transduce the hepatocytes of the animal of interest, e.g., mice in which the liver has been ablated with the urokinase gene as described herein and reconstituted with human hepatocytes. For example, scid mice that have livers reconstituted with human hepatocytes are infused with hepatitis C particles, or human HCV-infected hepatocytes are used in the reconstitution process. The liver and serum of the animals are monitored for production of virus by quantitative RT-PCR assays. Additionally, immunohistochemical staining of tissues or antigen detection in the blood can be performed. The ribozyme-expressing adenovirus is delivered to the animal and efficacy of HCV inhibition observed.

The following Examples are offered by way of illustration, not limitation.

EXAMPLE I

This Example describes the construction of an expression unit for a ribozyme library so as to achieve a high level of expression and stability of the expressed ribozyme.

Construction and Function of the Expression Cassette

To construct the ribozyme expression vector, oligonucleotides were synthesized in an automatic synthesizer (Applied Biosystems). The genes for vaRNAs I and II were cloned as an XbaI-NsiI fragment (Akusjarvi et al., *Proc. Natl. Acad. Sci. USA* 77: 2424–2428 (1980)) in the XbaI-PstI site of pGEM7zf+ after prior deletion of the AatII site in pGEM. The resulting plasmid was named pGva. Oligonucleotides I 5'CGTCGACTGCTGCAGTGCAGCGTGTG-GACCCAACGACACGCGGGCGGTAACCGACGT3' [Seq ID:7] and II 5'CGGTTACCGCCCGCGTGTCGT-TGGGTCCACACGCTGCACTGCAGCAGTC-GACGACGT3' [Seq ID:8], (10 ng each), which represent both strands of the sequence to form a loop, were annealed in 20 mM Tris-HCl (pH 7.5)–10 mM $MgCl_2$ by heating for 5 min. at 85° C. and slow cooling to room temperature and cloned into the AatII site within the va gene sequence. The resulting plasmid was designated pGvaL. The 5' end of oligonucleotides III 5' CCGCTCGAG(N)$_{13}$CTGATGAGTCCGTGAGGACGAAA3' [Seq ID:9] and IV 5'TGCATGCAT(N)$_{11}$N$_G$TTTCGTCCTCACGGACTCATCAG3' [Seq ID:10], where $N_G$ is 40% C, 40% G, 10% T, and 10% A, for the randomly mutated ribozymes were phosphorylated with polynucleotide kinase.

Oligonucleotides III and IV (5 µg each) were heated for 5 min. at 85° C. in 20 mM Tris-HCl (pH 7.5)–10 mM $MgCl_2$ cooled to 65° C., and incubated with 200 µM deoxynucleoside triphosphates-(dNTPs) 2.5U of Taq polymerase for 30 min at 65° C. After phenol extraction and ethanol precipitation, the double-stranded oligonucleotides were digested with NsiI-XhoI overnight and cloned into the SaiII and PstI sites of pGvaL. Ligation products were transformed in highly competent ($10^{10}$ colonies per µg of DNA) *E. coli* DH5, and plasmid DNA from a pool of $10^{10}$ different individual clones was prepared. The ribozyme gene library was designated GvalRz. The corresponding RNAs were designated va, vaL and ValRz.

T7 polymerase-dependent in vitro transcription was performed by incubating 2 µg of DNA template, 12.5 µl of TKB (20 mM Tris-HCl [pH 7.9], 0.2 mM EDTA, 10 mM 2-mercaptoethanol, 0.1M KCl, 20% glycerol, 0.5 mM phenylmethysulfonyl fluoride, 10 mM $MgCl_2$), 10U of RNasin, 2.5 µl of 5 mM NTPs (or 5 mM ATP, GTP, and TTP plus 20 µCi of [$^{32}$P]CTP and 1 mM CTP), 5 mM $MgCl_2$, 2.5 Al of 10 mM dithiothreitol, 100U of T7 RNA polymerase (Biolabs) in a total volume of 25 µl at 37° C. for 60 min. After digestion with 23U of DNase I, the transcripts were purified twice by phenol extraction and ethanol precipitated. The amount of RNA synthesized was estimated after gel electrophoresis in an ethidium bromide-stained agarose gel calibrated with concentration markers. In a standard reaction, 5 to 8 µg of RNA per 25-µl reaction volume was synthesized.

Function and Stability of the Chimeric Ribozyme RNA

Cleavage reactions with ribozymes were performed in vitro. For analytical analysis, 100 nM ribozyme and 100 nM in vitro-transcribed substrate human growth hormone (hGH) RNA or HCV plus RNA (type 1α) were mixed in a 15-µl reaction volume containing 50 mM Tris (pH 7.5) and 1 mM EDTA. For heat denaturation, the mixture was boiled at 95° C. for 90 s and quickly cooled on ice. $MgCl_2$ (10 mM) was added, and the mixture was incubated at 37° C. for 30 or 60 min. The reaction was stopped by addition of an equal volume of stop solution (95% formamide, 20 mM EDTA, 0.05% bromphenol blue, 0.05% xylene cyanol), the mixture was heated at 95° C. for 2 min., and the products were analyzed in a 4 or 6% polyacrylamide-8M urea gel in Tris-borate EDTA buffer.

Total-cell RNA was extracted by the guanidinium-phenol method (Chomczynski and Sacchi, *Anal. Biochem.* 162:156–159 (1987)) or with the RNaid Plus Kit (Bio 101, La Jolla, Calif.). Total hGH-RNA was extracted from a hGH expressing cell line. Total HCV (type 1b)-RNA was extracted from HCV positive human liver.

For northern blot analysis, RNA samples were fractionated on a 1.5% agarose gel containing 2.2M formamide and transfected to Hybond N+ nylon membrane. Northern (RNA) hybridization was carried out with $^{32}$P-labelled probes by the method described by Westneat et al., *Nucl. Acids. Res.* 16:4161–4170 (1988)). HCV and vaDNA sequences were labelled by standard random-priming techniques with DNA pol 1 (Klenow fragment).

Creation of a Functional R.ribozyme Library

Cleavage of cellular RNA in vitro by ribozymes from the library. Purified total-cell RNA was used as the source of mRNA.

Cleavage was carried out at physiological pH (50 mM Tris-HCl [pH 7.5]) at 37° C. for 1 h in a 15-µl reaction volume with or without prior heat denaturation (for 90 s at 95° C.). The cleavage products were analyzed in a 2% ethidium bromide-stained NuSieve agarose gel and could be detected as a smear between the 18S and 28S rRNAs and below the 18S rRNA. In some cases, the 5'—OH groups of cleavage products were phosphorylated with [$^{32}$P]ATP by using polynucleotide kinase and quantified on a Fuji Phosphorimager after polyacrylamide gel electrophoresis.

For the cleavage reaction purified total RNA (1 µg per reaction) and 10 µg of vaL (as control) or vaLRz (library) RNA, which were synthesized by T7 polymerase, were mixed and incubated in 50 mM Tris-HCl-10 mM $MgCl_2$ for 1 h at 37° C. with or without prior heat denaturation. No significant self-digestion of ribozymes was observed. The ribozyme cleavage was three times more efficient when the reaction mixture was heat denatured. Without addition of 10 mM $MgCl_2$, no specific cleavage reaction was detected. For further analyses, cleavage products were used without prior heat denaturation.

After the reaction, RNA was purified with oligo(dT)-cellulose (PolyATract mRNA Isolation System; Promega) according to the manufacturer's specifications. After purification, 0.05 to 0.5 µg of RNA was annealed with 2.5 µM oligo(dT) primer (Promega) for 10 min. at 70° C., and unbound primer was separated by centrifugation through a 30,000-molecular-weight-cutoff filter unit (Millipore). Reverse transcription was performed with 200U of superscript II reverse transcriptase (Bethesda Research Laboratories) at 37° C. for 1 h. To eliminate free primers, cDNA-RNA hybrids were purified with Gene Clean (Bio 101). The cDNA-RNA hybrid in 30 µl of $H_2O$ was boiled for 2 min. and cooled on ice. Tailing was carried out for 15 min. 37° C. in a total volume of 50 µl containing 200 µM dGTP, 20U of terminal deoxynucleotidyltransferase (Bethesda Research Laboratories), and tailing buffer.

A 5% portion of the tailing-reaction mixture was used for the first PCR with 200 µM dNTP, 1.5 mM $MgCl_2$, and 2.5 U of Taq polymerase in buffer containing 2% dimethyl sulfoxide, 50 mM KCl, 10 mM Tris-HCl (pH 7.9), and 0.1% Triton X-100 in a 100-µl reaction volume. The initial seven cycles (30 s at 95° C., 30 s at 42° C., and 90 s at 72° C.) were run in the presence of 15 µM C-Primer (5'GAGAATTCTAGAGGATCCCCCCCCCCCC3' [Seq ID:11]) only. After addition of 250 µM hGH-specific primer (5'GAGAATTCCAAGGCCAGGAGAGGCACTGGGGA3'

[Seq ID:12]), which is specific for a region immediately upstream of the poly(A) signal of the genomic hGH gene. PCR-primers for selecting HCV ribozymes are directed against sequences in the 5' untranslated region and core region of the HCV genome (see FIG. 2), and comprised: C1+: 5'GTAAACTCCACCAACGATCT [Seq ID:13]; C2+: 5'GAAGATAGAGAAAGAGCA [Seq ID:14]; C3+: 5'ACCCCATGAGGTCGGCGAA [Seq ID:15]; C1-: 5'CTGTGAGGAACTACTGT [Seq ID:16]; and C2-: 5'CACGCAGAAAGCGTCTAGCC [Seq ID:17]. PCR was done for 40 cycles (60 s at 94° C. and 90 s at 72° C. or 60 s at 95° C., 45 s at 65° C., and 60 s at 72° C.). The reaction mixture was run on a native 5% PAA gel in Tris-acetate buffer. HCV specific bands were identified by Southern blot with a 32P-labelled 730 bp fragment (XbaI/ClaI) of pTET/HCV5'T7G3'AFL (Lemm, Kolyakhov, Heise, Feinstone and Rice). Specific bands were cut out and purified with Gene Clean. The resulting fragments were cloned in the PGEM-T II vector system (Promega). Clones corresponding to the 5' end of individual RNA downstream cleavage products were sequenced with the fmole sequencing kit (Promega).

Identification of Specific Ribozymes in the Library

Amplification of ribozymes. Ribozyme genes from the library were amplified as follows. PCR was performed by incubating 50 ng of plasmids from the ribozyme library, 20 μM each upstream and downstream primer (which are specific for the sequences around the GTC/CTC site and 2.5 U of Taq polymerase in buffer containing 2% dimethyl sulfoxide, 50 mM KCl, 10 mM Tris-HCl (pH 7.9), and 0.1% Triton X-100 in a 100-μl reaction volume for 40 cycles (45 s 95° C., 45 s at 52° C., and 45 s at 72° C.). Specific fragments were prepared as described above, digested with XhoI-NsiI, cloned into the SaiII and PstI sites of GvaL, and sequenced with the T7 promoter primer.

Cell culture. Cells were grown in Dulbecco's modified Eagle's medium containing 200 mM asparagine, 200 mM proline, 200 mM glutamine, and 10% fetal calf serum (GIBCO, Grand Island, N.Y.) under a 5% $CO_2$ atmosphere.

Transfection. Plasmids were purified by two rounds of cesium chloride gradient centrifugation. For transfection of CHO cells, a modification of the standard calcium phosphate coprecipitation method was used (Lieber et al., *Nucleic Acids Res.* 17:8485–8493 (1989)). DNA (10 μg) in 220 μl of $H_2O$ was mixed with 30 μl of 2M $CaCl_2$ and 250 μl of 2×HBS (50 mM HEPES, 280 mM NaCl, 1.5 mM sodium phosphate [equal amounts of mono- and dibasic] [pH 6.96] was added dropwise while the mixture was vortexed. The precipitate was added to 5 mL of culture medium in 25-cm$^2$ tissue culture flasks containing 2.5×10$^5$ CHD cells that had been seeded the day before. Cells were transfected with a mixture of 8 μg of pTET HCV (Lemm et al., supra) test plasmid, and 1 μg of pSV2neo (Southern and Berg, *J. Mol. Appl. Genet.* 1: 327–341 (1982)). After 48h, ¹⁄₁₀ of the cells were subjected to selection with 600 μg of G418 per ml to generate pools of about 100 colonies in order to test for stable expression levels. The cell line was named HCV-CHO.

Figure 1:
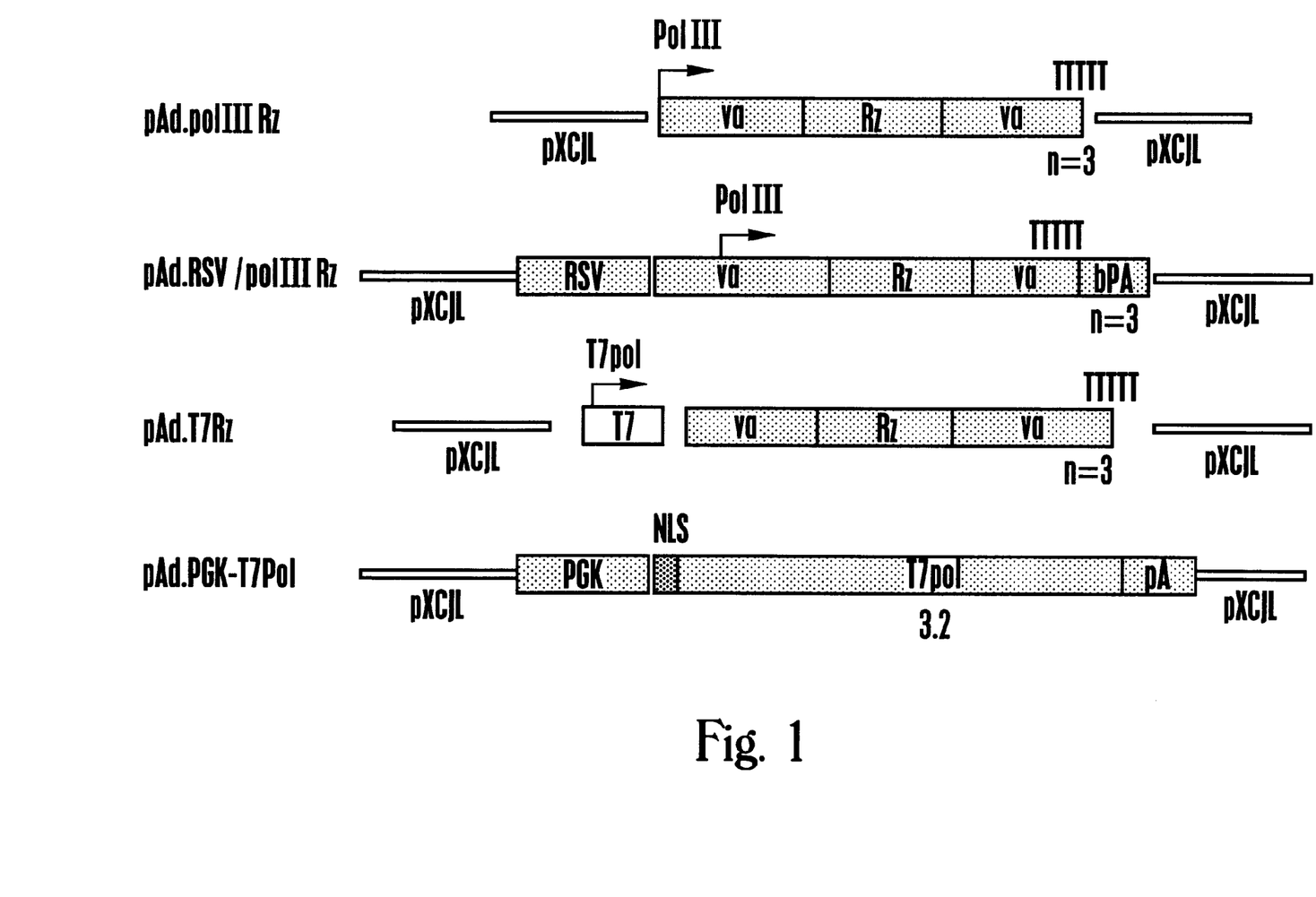
FIG. 1 shows adenovirus ribozyme expression cassettes. The ribozymes are cloned into the pXCJL.1 plasmid to produce the recombinant adenovirus vectors. The promoters used to drive expression of the ribozymes (Rz) are also shown.
Figure 2:
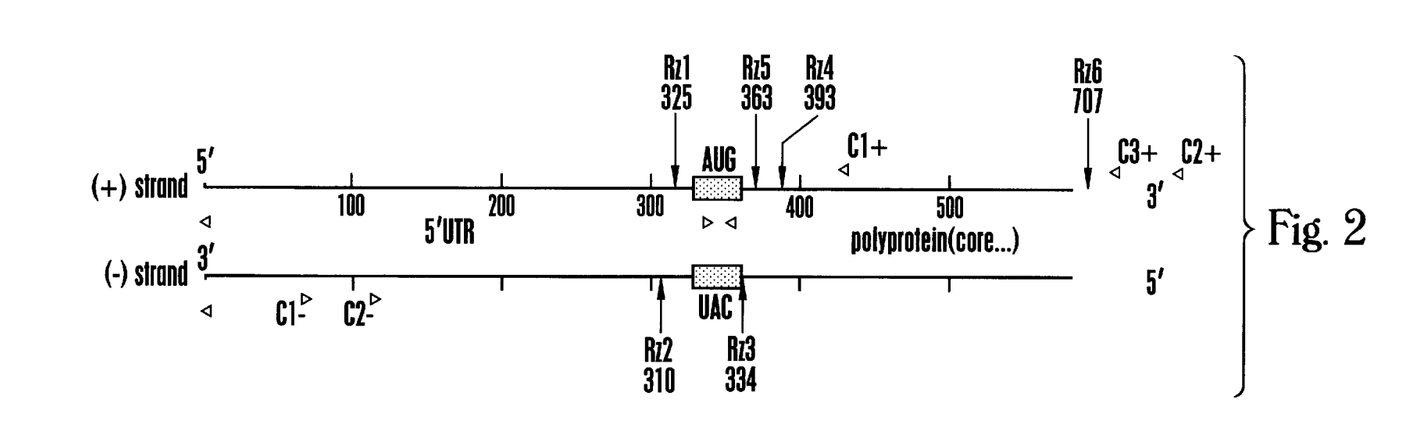
FIG. 2 shows cleavage sites for HCV ribozymes Rz1–Rz6 on the HCV RNA plus and minus strands.

Six ribozymes specific for HCV types 1a and 1b RNA were identified using the above described protocol. FIG. 2 shows cleavage sites for the HCV ribozymes, Rz1–Rz6, on the HCV RNA plus and minus strands. The HCV ribozyme target sequences are as follows, based on a cDNA sequence that corresponds to the HCV type 1a and type 1b RNA, where the putative ribozyme cleavage sites are indicated by a "–": ribozyme 1 (Rz1): CGGGAGGTCTCGTA [Seq ID:1] (5' UTR, nucleotides 317 to 332; plus strand), Rz2: GCAC-CATGAGCACGAA [Seq ID:2] (nucleotide 337 to 352; minus strand), Rz5: CTAAACCTCAAAGAAA [Seq ID:3] (core, nucleotide 355 to 370; plus strand), Rz4: CCAAC-CGTCGCCCACAG [Seq ID:4] (core, nucleotide 385 to 401; plus strand), Rz3: CCCACAGGACGTCAAG [Seq ID:5] (core, nucleotide 385 to 410; minus strand), and Rz6: GGTAAGGTCATCGATA [Seq ID:6] (core, nucleotide 699 to 714; plus strand).

EXAMPLE II

Ribozyme-Mediated Inhibition of HCV RNA

Figure 3:
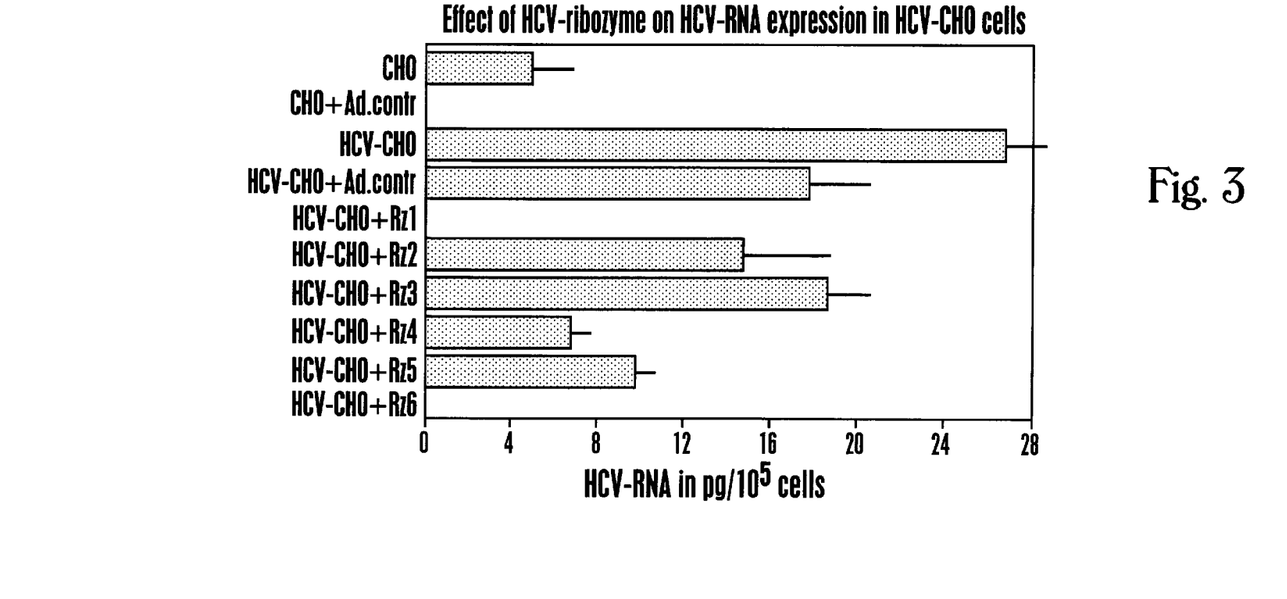
FIG. 3 shows the effect of adenovirus-mediated gene transfer of HCV ribozymes into HCV-RNA cell lines. The values represent the mean and standard deviations for five different experiments. Ribozymes 2 and 3 are directed against the negative HCV RNA strand and have no specific effect on plus strand HCV RNA concentrations.

Sequences encoding the HCV-specific ribozymes were cloned into the pXCJL.1 plasmid (Spessot et al., *Virology* 168:378–387 (1989)) to produce recombinant adenovirus vectors. The effect of adenovirus-mediated gene transfer of the HCV ribozymes on HCV RNA in an HCV-RNA expressing cell line was then determined. 1×10$^6$ CHO cells that express about 200 copies of plus strand HCV RNA per cell were incubated for 4 hrs. with 1000 pfu/cell of recombinant adenovirus vectors (the amount of virus that transduces 100% of CHO cells) that express ribozymes 1 through 6 or an irrelevant control vector. Forty hours later, total nucleic acid was extracted from harvested cells and HCV specific RNA was quantified by solution hybridization with an oligonucleotide specific for HCV type 1 a (nt 324–352) within the 5' NCR. The results are shown in FIG. 3, where the values represent the mean and standard deviations for five different experiments. A minor non-specific HCV signal was seen in normal CHO cells, and transduction with an irrelevant control resulted in a minor reduction in HCV RNA signal. Ribozymes 2 and 3 are directed against the negative HCV RNA strand and had no specific effect on plus strand HCV RNA concentrations.

EXAMPLE III

Ribozyme-Mediated Inhibition of hGH in Transgenic Animals

Figure 4A:
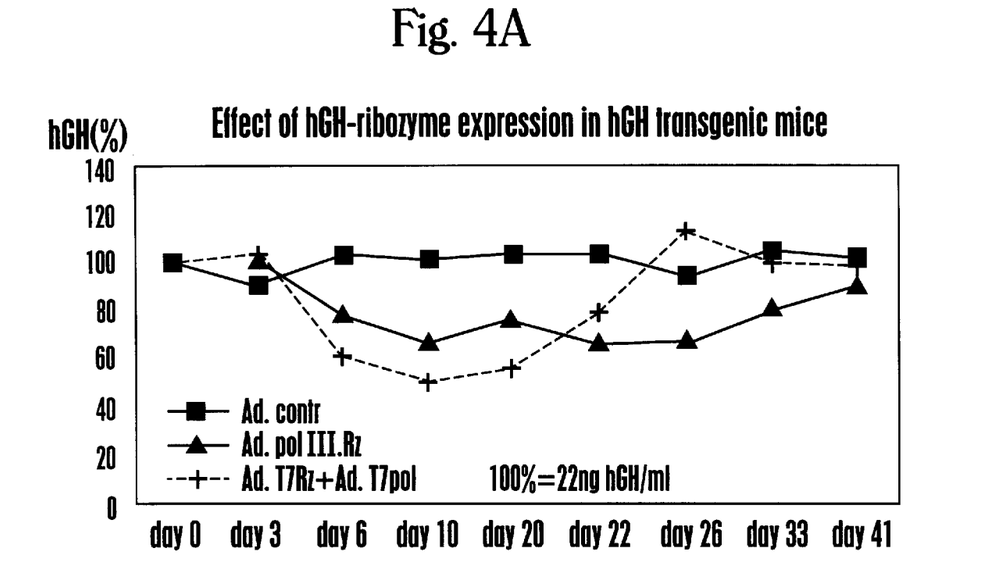
FIG. 4A shows the concentration of human growth hormone serum concentrations in hGH-transgenic mice after ribozyme therapy. Serum samples were analyzed for growth hormone by ELISA analysis at varying times after recombinant adenovirus administration.
Figure 4B:
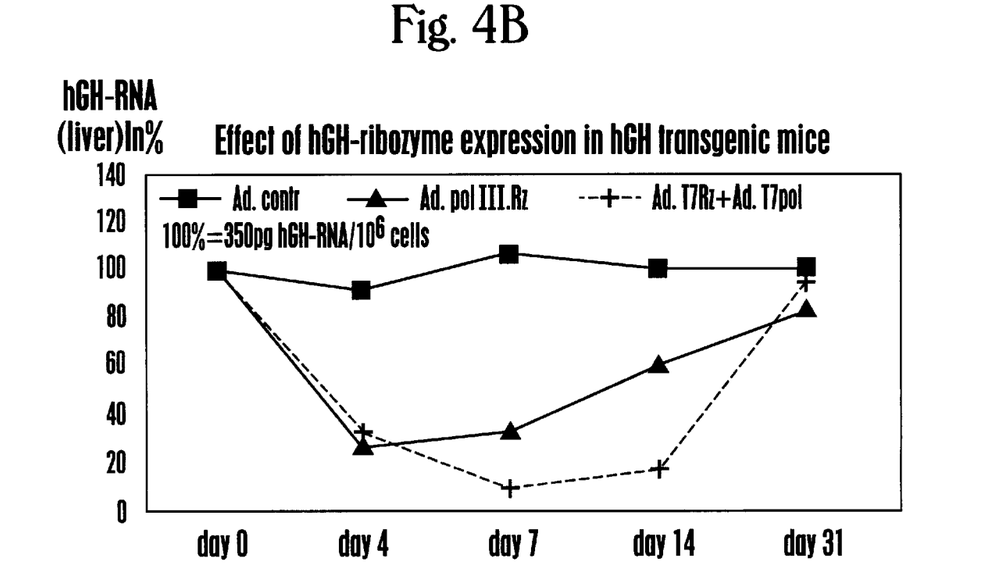
FIG. 4B shows hepatic mRNA quantitation in transgenic mice after ribozyme therapy. Ad/RSVhAAT is a control vector; Ad.polIII.Rz is adenovirus containing the hGH ribozyme driven by the adenovirus vaI promoter; Ad.T7Rz+ Ad.T7 pol is a 1:1 mixture of the adenovirus expressing nuclear T7 polymerase from the PGK promoter and an adenovirus containing the T7 promoter used to drive transcription of the hGH ribozyme.

To confirm that sequence specific ribozymes can be targeted to the liver for expression in animals, transgenic mice were created that expressed human growth hormone (hGH) and then treated with adenovirus vectors capable of expressing hGH-specific ribozymes. FIG. 4A shows the concentration of hGH serum concentrations in hGH-transgenic mice after ribozyme therapy, where hGH levels were estimated by enzyme-linked immunosorbent assay (ELISA) as described in Lieber et al., *Meth. Enzymol.* 217: 47–66 (1993)). Serum samples were analyzed for growth hormone at varying times after recombinant adenovirus administration. FIG. 4B shows hepatic mRNA quantitation in transgenic mice after ribozyme therapy, where hepatic mRNA levels were determined by solution hybridization (Townes et al., 1985; Durnam and Palmiter, 1983). Ad/RSVhAAT was used as a control vector, Ad.polIII.Rz is adenovirus containing the hGH ribozyme driven by the adenovirus vaI promoter, and Ad.T7Rz+Ad.T7 pol is a 1:1 mixture of the adenovirus expressing nuclear T7 polymerase from the PGK promoter and an adenovirus containing the T7 promoter used to drive transcription of the hGH ribozyme, (Lieber et al., *Meth. Enzymol.* 217:47–66 (1993)). The effective inhibition of hGH by the adenovirus encoding the hGH-specific ribozyme indicates that HCV-specific ribozymes can also be effective in vivo in inhibiting HCV RNA.

All publications, patents and foreign patent publications are herein incorporated by reference to the same extent as if each individual publication, patent or patent publication was specifically and individually indicated to be incorporated herein by reference.

Although the foregoing invention has been described in some detail by way of illustration and example for purposes of clarity of understanding, it will be readily apparent that certain changes and modifications may be practiced within the scope of the appended claims.

What is claimed is:

1. A method for inhibiting hepatitis C virus RNA in cells comprising:
   transducing said cells with a recombinant adenovirus which encodes a ribozyme specific for a minus strand hepatitis C virus 5' non-coding sequence of hepatitis C virus RNA, and maintaining the transduced cells under conditions whereby the ribozyme is expressed and inhibits the hepatitis C virus RNA.

2. The method of claim 1, wherein the cells are hepatocytes.

3. The method of claim 2, wherein the hepatocytes are a hepatoma cell line.

4. The method of claim 2, wherein the hepatocytes are from an HCV-infected individual.

5. The method of claim 2, wherein the infected hepatocytes are in an individual infected with hepatitis C virus.

6. The method of claim 5, wherein the transducing step comprises administering said recombinant adenovirus to the individual by infusion.

7. The method of claim 6, wherein the infusion is via the portal vein or bile duct.

8. The method of claim 1, wherein the ribozyme is a hammerhead ribozyme.

9. The method of claim 1, wherein the ribozyme is selected from a ribozyme specific for an HCV RNA transcript corresponding to a cDNA sequence comprising [CGGGAGGTCTCGTA [SEQ ID NO: 1] (nucleotide 317 to 332),] GCACCATGAGCACGAA [[SEQ ID NO: 2]] (SEQ ID NO:2: nucleotide 337 to 352)[, CTAAACCTCAAAGAAA [SEQ ID NO: 3] (nucleotide 355 to 370), CCAACCGTCGCCCACAG [SEQ ID NO: 4] (nucleotide 385 to 401),] or CCCACAGGACGTCAAG [SEQ ID NO: 5] (SEQ ID NO:5: nucleotide 385 to 3410)[ or GGTAAGGTCATCGATA [SEQ ID NO: 6] (nucleotide 699 to 714)].

10. The method of claim 1, wherein the adenoviral vector encodes at least two ribozymes specific for hepatitis C virus mRNA.

11. The method of claim 1, wherein the recombinant adenovirus is administered to the hepatocytes in an amount of from 10 to 100 adenovirus particles per hepatocyte.

12. The method of claim 1, wherein the recombinant adenovirus is administered to the hepatocytes in an amount and for a time sufficient to eradicate hepatitis C virus from the hepatocytes.

13. The method of claim 1, wherein the recombinant adenovirus further comprises a ligand specific for a receptor on said hepatocytes.

14. A composition for inhibiting hepatitis C virus RNA in a cell, which comprises a recombinant adenovirus encoding at least one ribozyme specific for a minus strand hepatitis C virus 5' non-coding sequence of hepatitis C virus RNA.

15. The composition of claim 14, wherein the recombinant adenovirus encodes two different ribozymes specific for hepatitis C virus RNA.

16. The composition of claim 14, wherein the ribozyme is a hammerhead ribozyme.

17. The composition of claim 14, wherein the ribozyme is specific for a HCV RNA transcript corresponding to a cDNA sequence comprising [CGGGAGGTCTCGTA [SEQ ID NO: 1] (nucleotide 317 to 332),] GCACCATGAGCACGAA [[SEQ ID NO: 2]] (SEQ ID NO: nucleotide 337 to 352)[, CTAAACCTCAAAGAAA [SEQ ID NO: 3] (nucleotide 355 to 370), CCAACCGTCGCCCACAG [SEQ ID NO: 4] (nucleotide 385 to 401),] or CCCACACGACGT-CAAG [SEQ ID NO: 5] (SEQ ID NO:5: nucleotide 385 to 410)[ or GGTAAGGTCATCGATA [SEQ ID NO: 6] (nucleotide 699 to 714)].

18. A composition which comprises a ribozyme specific for an HCV RNA transcript corresponding to a cDNA sequence comprising CGGGAGGTCTCGTA [[SEQ ID NO: 1]] (SEQ ID NO:1; nucleotide 317 to 332), GCACCATGAGCACGAA [[SEQ ID NO: 2]] (SEQ ID NO:2; nucleotide 337 to 352), CTAAACCTCAAAGAAA [[SEQ ID NO: 3]] (SEQ ID NO:3: nucleotide 355 to 370), CCAACCGTCGCCCACAG [[SEQ ID NO: 4]] (SEQ ID NO:4; nucleotide 385 to 401), CCCACAGGACGTCAAG [[SEQ ID NO: 5]] (SEQ ID NO:5; nucleotide 385 to 410) or GGTAAGGTCATCGATA [[SEQ ID NO: 6]] (SEQ ID NO:6: nucleotide 699 to 714).

19. A composition for inhibiting hepatitis C virus RNA in a cell, which comprises a recombinant adenovirus encoding at least one ribozyme specific for hepatitis C virus RNA, wherein said ribozyme is selected from the group consisting of CGGGAGGTCTCGTA (SEQ ID NO:1), CTAAACCT-CAAAGAAA (SEQ ID NO: 3), CCAACCGTCGCCCA-CAG (SEQ ID NO: 4) and GGTAAGGTCATCGATA (SEQ ID NO:6).

* * * * *

UNITED STATES PATENT AND TRADEMARK OFFICE
CERTIFICATE OF CORRECTION

PATENT NO.   : 6,107,027
DATED        : August 22, 2000
INVENTOR(S)  : Kay et al.

It is certified that error appears in the above-identified patent and that said Letters Patent is hereby corrected as shown below:

Column 4,
Line 52, please delete "18: 299" and replace therefor with -- 18(2):299-304 --.
Line 54, please delete "31: 16" and replace therefor with -- 31:16-21 --.

Column 7,
Line 50, please delete "a enzyme." and replace therefor with -- an enzyme. --.

Column 10,
Line 2, please delete "used to as" and replace therefor with -- used as --.

Column 12,
Line 19, please delete "R.ribozyme" and replace therefor with -- Ribozyme --.

Column 14,
Line 21, please delete "1 a" and replace therefor with -- 1a --.

Column 22,
Lines 38-46, please delete

"[CGGGAGGTCTCGTA [SEQ ID NO: 1] (nucleotide 317 to 332),] GCACCATGAGCACGAA [[SEQ ID NO: 2]] (SEQ ID NO: nucleotide 337 to 352)[, CTAAACCTCAAAGAAA [SEQ ID NO: 3] (nucleotide 355 to 370), CCAACCGTCGCCCACAG [SEQ ID NO: 4] (nucleotide 385 to 401),] or CCCACACGACGTCAAG [SEQ ID NO: 5] (SEQ ID NO:5: nucleotide 385 to 410)[ or GGTAAGGTCATCGATA [SEQ ID NO: 6] (nucleotide 699 to 714)]." and replace therefor with --CGGGAGGTCTCGTA [SEQ ID NO: 1] (nucleotide 317 to 332), GCACCATGAGCACGAA [SEQ ID NO: 2] (nucleotide 337 to 352), CTAAACCTCAAAGAAA [SEQ ID NO: 3] (nucleotide 355 to 370), CCAACCGTCGCCCACAG [SEQ ID NO: 4] (nucleotide 385 to 401), CCCACACGACGTCAAG [SEQ ID NO: 5] (nucleotide 385 to 410); or, GGTAAGGTCATCGATA [SEQ ID NO: 6] (nucleotide 699 to 714).--.

UNITED STATES PATENT AND TRADEMARK OFFICE
CERTIFICATE OF CORRECTION

PATENT NO. : 6,107,027
DATED : August 22, 2000
INVENTOR(S) : Kay et al.

It is certified that error appears in the above-identified patent and that said Letters Patent is hereby corrected as shown below:

<u>Column 22 cont'd,</u>
Lines 49-58, please delete

"sequence comprising

CGGGAGGTCTCGTA [[SEQ ID NO. 1]] (SEQ ID NO:1; nucleotide 317 to 332),

GCACCATGAGCACGAA [[SEQ ID NO: 2]] (SEQ ID NO:2; nucleotide 337 to 352),

CTAAACCTCAAAGAAA [[SEQ ID NO: 3]] (SEQ ID NO:3: nucleotide 355 to 370),

CCAACCGTCGCCCACAG [[SEQ ID NO: 4]] (SEQ ID NO:4; nucleotide 385 to 401),

CCCACAGGACGTCAAG [[SEQ ID NO: 5]] (SEQ ID NO:5; nucleotide 385 to 410) or

GGTAAGGTCATCGATA [[SEQ ID NO. 6]] (SEQ ID NO:6: nucleotide 699 to 714)." and replace therefor with --sequence comprising CGGGAGGTCTCGTA [SEQ ID NO: 1]

(nucleotide 317 to 332), GCACCATGAGCACGAA [SEQ ID NO: 2] (nucleotide 337 to 352), CTAAACCTCAAAGAAA [SEQ ID NO: 3] (nucleotide 355 to 370), CCAACCGTCGCCCACAG [SEQ ID NO: 4] (nucleotide 385 to 401), CCCACAGGACGTCAAG [SEQ ID NO: 5] (nucleotide 385 to 410); or, GGTAAGGTCATCGATA [SEQ ID NO. 6] (nucleotide 699 to 714).--.

Signed and Sealed this

Twenty-fourth Day of February, 2004

JON W. DUDAS
*Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:1:

CGGGAGGTCT CGTA                                                   14

(2) INFORMATION FOR SEQ ID NO:2:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:2:

GCACCATGAG CACGAA                                                 16

(2) INFORMATION FOR SEQ ID NO:3:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:3:

CTAAACCTCA AAGAAA                                                 16

(2) INFORMATION FOR SEQ ID NO:4:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:4:

CCAACCGTCG CCCACAG                                                17

(2) INFORMATION FOR SEQ ID NO:5:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:5:

```
CCCACAGGAC GTCAAG                                              16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

GGTAAGGTCA TCGATA                                              16

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:7:

CGTCGACTGC TGCAGTGCAG CGTGTGGACC CAACGACACG CGGGCGGTAA CCGACGT       57

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:8:

CGGTTACCGC CCGCGTGTCG TTGGGTCCAC ACGCTGCACT GCAGCAGTCG ACGACGT       57

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

CCGCTCGAGN NNNNNNNNNN NNCTGATGAG TCCGTGAGGA CGAAA                    45

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:10:

TGCATGCATN NNNNNNNNNN NTTTCGTCCT CACGGACTCA TCAG                     44
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

GAGAATTCTA GAGGATCCCC CCCCCCCC                                  28

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:12:

GAGAATTCCA AGGCCAGGAG AGGCACTGGG GA                             32

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:13:

GTAAACTCCA CCAACGATCT                                           20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:14:

GAAGATAGAG AAAGAGCA                                             18

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:15:

ACCCCATGAG GTCGGCGAA                                            19

(2) INFORMATION FOR SEQ ID NO:16:

(i) SEQUENCE CHARACTERISTICS:
        (A) LENGTH: 17 base pairs

```
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:16:

CTGTGAGGAA CTACTGT                                                    17

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:17:

CACGCAGAAA GCGTCTAGCC                                                 20
```